United States Patent [19]
Zimmermann et al.

[11] Patent Number: 5,338,677
[45] Date of Patent: Aug. 16, 1994

[54] **HEPARINASE FREE OF AN ANTICOAGULANT COMPONENT FROM *FLAVOBACTERIUM HEPARINUM***

[75] Inventors: Joseph J. Zimmermann, Elm Grove, Wis.; N. Tracey Lewis, Brossard; Robert A. Heft, Ville St. Laurent, both of Canada

[73] Assignee: Ibex Technologies, Inc., Montreal, Canada

[21] Appl. No.: 153,134

[22] Filed: Nov. 15, 1993

Related U.S. Application Data

[62] Division of Ser. No. 680,330, Apr. 4, 1991, Pat. No. 5,262,325.

[51] Int. Cl.$^5$ .......................... C12N 9/24; C12N 1/12; C12N 1/00
[52] U.S. Cl. .................................. 435/200; 435/252.1; 435/850
[58] Field of Search ...................... 435/200, 252.1, 850

[56] References Cited

U.S. PATENT DOCUMENTS

| | | | |
|---|---|---|---|
| 3,950,133 | 4/1976 | Monte et al. | 435/187 |
| 4,795,703 | 1/1989 | Folkman et al. | 435/13 |

OTHER PUBLICATIONS

Lindahl, et al., "Biosynthesis of Heparin" TIBS 11(5):221-225, (1986).

Sakamoto, et al., "Heparin and bone Metabolism: Effects of heparin on bone collagenase release and activity and an application of heparin-sepharose affiity chromatography for in vitro study of bone resorption" *Chemistry and Biology of Heparin*) (Elsevier/North Holland Press, Amsterdam 1981).

Rosenberg, et al., "The purification and mechanism of action of the human anti-thrombin-heparin cofactor", *J. Biol. Chem.*, 248:6490-6505.

Choay, J., et al., "Anti-Xa active heparin oligosaccharides" *Thrombosis Res.*, 11:240, 1980.

Cumming, A. M. et al., "In vitro neutralization of heparin in plasma prior to the activated partial thromboplastin time test; an assessment of four heparin antagonists and two anion exchange resins" *Thrombosis Res.*, 41:43-56.

Funk, C., et al., "Reptilase-R-a new reagent in blood coagulation" *Brit. J. Haematol.*, 21:43-52.

Hutt, Ed, et al., "Use of Heparinase to eliminate heparin inhibition in routine coagulation assays" J. Lab. Clin. Med. 79:1027, 1972.

Akoum, A., et al., "Anticoagulant activity of a bacterial glycopeptide" Thrombosis Res., 60:9-18.

Galliher, P. C., et al. "Heparinase production by Flavobacterium herpainum" Appl. Envir. Microbiol. 41(2):360-365.

Bohmer, L. H., et al., "Heparin degradation by a novel heparinase" *Thrombosis Res.* 60:331-335.

Klein, et al., "Heparinase. Invivo activity and immunogenecity in rabbits" J. Lab Clin Med, 102:8280837.

Langer, et al., "In vivo activity of microbial heparinase" Trans Am Soc Artific Intern Organs, 28:387-390.

Fabian, et al. "Polycations as Possible Substitutes for Protamine in Heparin Neutralization", *Thrombosis Research*, 17:239-247, (Pergamon Press Ltd. 1980).

Lander, et al., "An Enzymatic System for Removing Heparin in Extra-Corporeal Therapy", *Science*, vol. 271, 261-263, (Jul. 16, 1982).

Dixon et al., Enzymes, Fractionation Methods, p. 39, 1964.

*Primary Examiner*—David M. Naff
*Assistant Examiner*—Michael V. Meller
*Attorney, Agent, or Firm*—Kilpatrick & Cody

[57] ABSTRACT

A heparinase derived from *Flavobacterium heparinum* which meets all requirements for a clinical reagent that can eliminate heparin interference of normal blood function has been developed. The heparinase, derived from *Flavobacterium heparinum*, is free of a component that inhibits coagulation wherein the anticoagulant component does not bind, and the heparinase does bind, to a polysulfated resin having a pH of 7.0 and a conductivity between 3 and 12 mmhos. It is stable under normal manufacturing, shipping and clinical storage conditions for at least one year. The heparinase in useful in vitro to eliminate the interference in hematological assays due to the presence of heparin. The heparinase is also useful for the in vivo neutralization of heparin during surgical procedures. Advantages of this enzyme are that it achieves neutralization faster and more completely than previously available enzymes and is stable for long periods of time.

6 Claims, 1 Drawing Sheet

HEPARINASE FREE OF AN ANTICOAGULANT COMPONENT FROM *FLAVOBACTERIUM HEPARINUM*

This is a divisional of copending U.S. Ser. No. 07/680,330 entitled "Method for the Enzymatic Neutralization of Heparin (as amended)" filed in the U.S. Patent & Trademark Office by Joseph J. Zimmermann, N. Tracey Lewis and Robert A. Heft on Apr. 4, 1991, now U.S. Pat. No. 5,262,325.

BACKGROUND OF THE INVENTION

This invention relates to a method for treating mammalian blood and plasma with a commercially viable bacterial heparinase preparation to eliminate the interference of normal blood function resulting from the presence of heparin.

Heparin is a sulfated glycosaminoglycan with a backbone comprised of alternating hexuronic, either L-iduronic or D-glucuronic and D-glycocyamine residues joined in alternating 1,4 linkages. The heterologous nature of heparin is due to the varying degree and location of sulfate substitution on these residues giving rise to at least ten different monosaccharide building blocks within the polymer, as reported by Lindahl, et al., *Biosynthesis of heparin TIBS* 11(5):221–225 (1986). The heterogeneity and high degree of sulfate substitution, greater than 2.6 sulfates per disaccharide unit, gives heparin a high protein binding capacity resulting in the inhibition or activation of several enzyme systems (Sakamoto and Sakamoto, "Heparin and bone metabolism: Effects of heparin on bone collagenase release and activity and an application of heparin-sepharose affinity chromatography for in vitro study of bone resorption" in *Chemistry and Biology of Heparin* (Elsevier/North Holland Press, Amsterdam 1981)). Protein-heparin associations are most frequently due to electrostatic interactions although associations due to tertiary and secondary structure interactions corresponding with specific oligosaccharide sequence regions have also been observed. The most thoroughly studied sequence specific interaction is the stabilization of the antithrombin 3 (AT III)—thrombin complex which results in the inhibition of coagulation, as discussed by Rosenberg and Damus, *J. Biol. Chem.* 248:6490–6505 (1973).

Heparin is widely used as an anticoagulant in conjunction with invasive surgical procedures and dialysis procedures, to prevent clotting in intravenous lines and in the treatment of thrombolytic disorders. 5–10% of all hospitalized patients have heparin in their blood. Recently, low molecular weight heparins, chemical derivatives of native heparin, have been investigated as potential anticoagulants where the primary mechanism of action is the inhibition of factor Xa, as reported by Choay, et al., *Thrombosis Res.* 11:240 (1980).

Patients receiving heparin therapy or who have been exposed to heparin through intravenous lines are frequently tested by a variety of means for the assessment of their hematological status or to monitor heparin therapy, itself. For example, activated clotting time assays are performed at 20 minute intervals during extracorporeal procedures to ensure adequate heparinization and the prevention of contact activated clotting. Heparin interferes with several routine hematological analyses. The presence of heparin in the bloodstream will prevent the identification of coagulopathies by standard coagulation assays which rely on clotting as the endpoint. These include activated partial thromboplastin time, prothrombin time, factor compliment assays and activated clotting time. Heparin's electrostatic interactions with essential components of other tests, such as the polylysine substrate in the fibrinolysis assay, causes similar interference problems.

Several approaches have been attempted to circumvent the heparin interference problem. Ion exchange resins have been used to adsorb heparin from the sample prior to testing, as described by Cumming, et al., *Thrombosis Res,* 41:43–56 (1986). This method is nonspecific, removing coagulation factors and other blood proteins in addition to heparin, thereby influencing the test result. The technique is also time consuming and cannot be readily used as a STAT test during surgery where rapid data acquisition is necessary.

Protamine sulfate has been used to neutralize heparin by electrostatic interaction and precipitation, as also reported by Cumming, etal., (1986). The protamine-heparin reaction is stoichiometric and requires an accurate titration to prevent adverse effects resulting from incomplete neutralization or from protamine sulfate's own anticoagulant properties. This method is cumbersome, prone to error and requires large sample volumes for accurate titration measurements. Protamine sulfate is not able to neutralize the anticoagulant effect of low molecular weight heparins.

Another approach is to supplement inhibited thrombin with additional thrombin or a substitute enzyme, such as reptilase, capable of catalyzing a similar reaction, as described by Funk, et al., *Brit. J. Haematol.* 21:43–52 (1971). This method may be successful for assays intended to monitor events subsequent to fibrin formation but is unsuitable for detecting coagulopathies in the coagulation pathway prior to the thrombin catalyzed reaction. Furthermore, heparin's effects on other components such as platelets, cannot be circumvented by these replacement enzymes.

The most desirable resolution to the heparin interference problem would be a method that could expeditiously and specifically remove heparin from blood samples immediately before the onset of the test. The additive used to accomplish this must function over a broad range of conditions. Heparin should be neutralized, nearly instantaneously, while the reagent, itself, should not impart any effects on blood components over a lengthy exposure period. A reagent demonstrating these characteristics could be used in conjunction with ACT assays which are performed immediately after sample procurement and on samples examined in the hematology laboratory which are liable to sit on the bench for up to one hour before processing. The reagent must function over a broad temperature range, 2° to 37° C., to accomodate samples including: those stored on ice in the hematology laboratory, samples taken from patients undergoing cardiovascular surgery whose blood temperature is maintained at 30° C. and samples from patients undergoing procedures such as dialysis which are carried out at normal body temperatures, 37° C. The heparin neutralizing reagent should also be concentration independent such that a single does of the reagent will effectively neutralize a broad range of heparin concentrations exceeding clinically used quantities (up to 0.3 IU/ml for thrombolytic therapy, up to 1.5 IU/ml for dialysis therapy, and up to 6 IU/ml for cardiovascular surgery). Furthermore, the treated samples containing heparin should give a result identical to untreated samples that have not been exposed to heparin. A candidate reagent would be a degradative glucanase enzyme specific for heparin which had no other effect on the sample as measured by the intended test.

Hurt and Kingdon, *J. Lab. Clin. Med.* 79:1027 (1972), attempted to use a heparinase from *Flavobacterium heparinum* to treat plasma samples prior to performing PTT analysis. The authors noted the requirement for purifying the heparinase from crude extracts of *F. heparinum* to reduce an interference effect from the bacterial source. However, their data indicated their inability to completely remove the interfering moiety. A protein preparation containing 0,008 IU heparinase was insufficient in neutralizing 0.1 IU/ml heparin while a preparation containing 0.04 IU heparinase caused an extended PTT time. The success of this preparation relies on an accurate titration of the enzyme and would be limited in the amount of heparin that could be neutralized.

U.S. Pat. No. 4,795,703 to Folkman, et al, describes using heparinase from *F. heparinum* to develop a method for making quantitative heparin determinations in whole human blood samples using an activated clotting time assay. They were similarly unable to completely remove an interfering moiety from their enzyme preparations. Heparinase treated samples originally containing heparin demonstrated ACT times 16% longer than untreated samples that had not been exposed to heparin. This effect was not detrimental to their process as quantitative heparin determinations relied on comparing test results to a standard curve which presumably took into account the influence of the enzyme preparation on the test result.

Neither group identified the *F. heparinum* moiety responsible for influencing the test results nor demonstrated its resolution from the active *F. heparinum* component responsible for heparin neutralization. The authors of these papers could not differentiate whether their preparations contained an additional molecule from *F. heparinum* that acted as an anticoagulant or whether heparinase, itself, has anticoagulant properties when used in excess or in combination with heparin. The recent characterization of myxalin, a glycoprotein from a Gram negative bacterial source, demonstrates that it possesses anticoagulant properties associated with its carbohydrate moiety, as reported by Akoum, et al., *Thrombosis Res.* 60:9-18 (1990). Evidence strongly indicates that heparinase is also a glycoprotein, thereby substantiating its potential to have similar characteristics.

Bohmer, et al., *Thrombosis Res.* 60: 331-335 (1990) have used heparinase III from an undetermined, unavailable bacterial source to neutralize heparin prior to aPTT and PT assays and examined its potential to neutralize heparin's inhibition of thrombin mediated fibrinogen degradation. Incubations of the enzyme with citrated plasma at 37° C. for five minutes and with whole blood at 37° C. for 15 minutes were used to achieve the desired heparin neutralization. The optimal activity profile of heparinase III, pH 7.6, [NaCl]=0.03 and T=45° C. (16), may have necessitated the inclusion of an incubation period in the reported protocol.

Neither of these three groups presented evidence for the stability of their heparinase formulation, an essential component of a clinical product.

One of heparin's primary therapeutic uses is to prevent coagulation during cardiovascular surgery while the patient's blood is circulating through an extracorporeal circuit. Approximately ten times the normal thrombolytic dose of heparin is used in this application, requiring post-operative neutralization by the administration of protamine. Since protamine reversal is associated with several complications and requires titration, an alternative approach to the heparin/protamine control of hemostasis is desirable. One method may be to replace protamine reversal with heparinase, directly injected into the patient after bypass.

Langer and co-workers investigated the in vivo effects of heparinase in animal models, as reported by Klein, et al., *J. Lab. Clin. Med.* 102:828-837 (1982) and Langer, et al., *Trans. Am. Soc. Artific. Intern. Organs* 28:387-390 (1982). Heparinase with a specific activity of 0.58 IU/mg was injected into rabbits that had received heparin and aPTT assays were used to measure coagulation over time. An accelerated heparin clearance was noted as compared to rabbits which did not receive heparinase. However, coagulation times were still three times baseline, 15 minutes after the heparinase injection and returned to baseline only 1 h later, the same period of time for the control animal which did not receive a heparinase injection. Langer was able to achieve better reversal by pumping blood through an immobilized heparinase reactor. Following this result, the Langer group abandoned the idea of direct heparinase injection and focused on developing the extracorporeal use of heparinase to replace protamine.

It is therefore an object of the present invention to provide a heparinase preparation which can be used to quickly and completely neutralize heparin in a wide range of concentrations, both in vitro and in vivo.

It is a further object of the present invention to provide a heparinase preparation which is free of any contaminants altering coagulation times.

It is a still further object of the present invention to provide a heparinase preparation which is stable for an extended period of time at room temperature.

SUMMARY OF THE INVENTION

A heparinase formulation derived from *F. heparinum* which meets all requirements for a clinical reagent that can eliminate heparin interference of normal blood function has been developed. The heparinase, derived from *F. heparinum*, is free of a component that inhibits coagulation. It is stable under normal manufacturing, shipping and clinical storage conditions for at least one year. The heparinase has an optimal activity profile close to physiological conditions: pH=6.5 to 7.0; [NaCl]=0.1, and T=37° C. The preparation achieves the intended neutralization over a broad range of conditions encompassing all of those likely to be encountered in a clinical setting.

The heparinase in useful in vitro to eliminate the interference in hematological assays due to the presence of heparin. The heparinase is also useful for the in vivo neutralization of heparin during surgical procedures. Advantages of this preparation are that it achieves neutralization faster and more completely than previously available compositions and is stable for long periods of time.

DETAILED DESCRIPTION OF THE INVENTION

Figure 1:
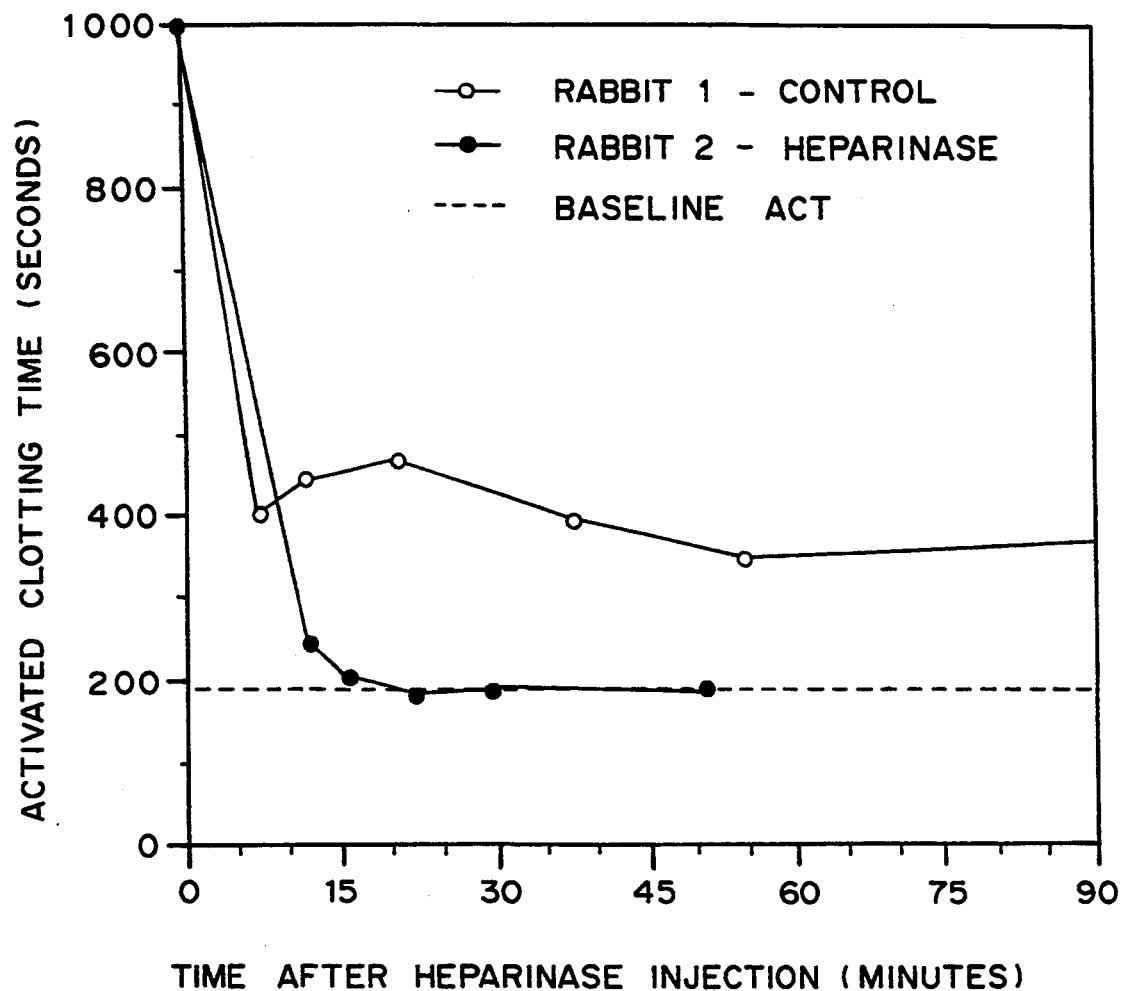
FIG. 1 is a graph of the activated clotting time (seconds) versus time after heparinase injection (minutes) for a control rabbit receiving 250 IU heparin/kg but not heparinase (open circles) and a rabbit receiving 250 IU heparin/kg followed five minutes later with 2.5 IU heparinase/kg (closed circles). The baseline ACT is indicated as (....) The ACT of the treated rabbits was monitored over ninety minutes.

A heparinase formulation derived from *F. heparinum* which meets all requirements for a clinical reagent that can eliminate heparin interference of normal blood function has been developed. Heparinase itself has been determined not to be an anticoagulant. In pursuing this aim, the heparinase from *F. heparinum* was completely separated from a component that inhibits coagulation. A method to formulate heparinase so that it is stable under normal manufacturing, shipping and clinical storage conditions for at least one year has also been developed. Heparinase from *F. heparinum* has an optimal activity profile which is closer to physiological conditions, rendering this enzyme suitable for the intended applications: pH=6.5 to 7.0; [NaCl]=0.1, and T=37° C. The preparation described herein achieves the intended neutralization over a broad range of conditions encompassing all of those likely to be encountered in a clinical setting. A comparison of the results shown herein with published information demonstrates that this purified, stabilized heparinase provides the first commercial enzymatically based product capable of resolving the heparin interference problem.

There are three operational components: (1) the preparation of anticoagulant free heparinase, (2) the stabilization and formulation of anticoagulant free heparinase, and (3) the use of anticoagulant free heparinase to eliminate the interference in hematological assays due to the presence of heparin. The heparinase is also useful for the in vivo neutralization of heparin during surgical procedures.

Preparation of anticoagulant free heparinase.

Heparinase is isolated from cultures of the Gram negative bacterium *Flavobacterium heparinum*. *F. heparinum* is grown in a suitable nutrient medium containing heparin to induce heparinase synthesis according to the method of Galliher, et al., *Appl. Environ. Microbiol.* 41(2):360–365 (1981) or a similar method. The *F. heparinum* cells are concentrated and the heparinase released into solution by sonication, homogenization or an osmotic shock technique. Heparinase is then purified from this solution by one or more of the standard purification methods including: protamine sulfate precipitation, ammonium sulfate precipitation, hydroxylapatite chromatography, anion exchange chromatography or cation exchange chromatography, to produce a preparation with a specific activity of between 10 and 35 IU heparinase/mg protein. This material contains a moiety that inhibits coagulation, as measured by the standard aPTT and ACT assays.

The material is further purified by an affinity chromatography step using cellufine sulfate (Amicon TM) or an equivalent polysulfated resin. The material is exposed to the resin under conditions in which the heparinase is adsorbed while the anticoagulant moiety remains in solution, for example, pH 7.0, conductivity between 3 to 12 mmhos. After washing the resin to thoroughly remove traces of the anticoaqulant moiety, the heparinase is recovered by washing in a buffer of increased conductivity, for example pH 7.0, conductivity greater than 16 mmhos. Functionally equivalent solutions can be substituted for the pH 7.0, 3 to 12 and greater than 16 mmho solutions. The heparinase fraction recovered is free of the contaminating anticoagulant moiety.

Heparinase clinical formulation.

Heparinase, stored in buffered salt solutions normally used to carry out the heparinase reaction, is reported by Langer, et al., *Science* 217:261–263 (1982), to have a half life of 1 h at 37° C., 30 h at 23° C. and 125 h at 4° C. As described below, several compounds have been examined for their ability to stabilize a soluble heparinase preparation. Of these, ammonium sulfate performed best, extending the enzymatic half life of heparinase 60 fold. High concentrations of sodium acetate and sodium sulfate also stabilized heparinase activity, but not to as great an extent as ammonium sulfate. The stabilizing agents, preferably the ammonium sulfate or other similar salt, are added to the heparinase in a ratio of 0.5–1.0 mg ammonium sulfate/IU anticoagulant free heparinase. Most clinical samples will contain in the range of 0.05 to 3.0 IU anticoagulant free heparinase.

Elimination of heparin interference.

An aliquot of freshly drawn whole blood or plasma recovered from blood is transferred into a tube containing the lyophilized heparinase preparation. The enzyme is allowed to dissolve into the sample and incubate for up to 60 minutes at 4°–37° C. In general, heparinase neutralization is complete within the time required for the enzyme to dissolve, less than 15 seconds. For example, 0.05 IU heparinase completely neutralizes the heparin in a 0.4 ml whole blood sample containing 4.8 IU heparin in 15 seconds.

After incubation the sample is ready for processing by the intended hematological assay. The assay may be processed using standard protocols. The result obtained will be equivalent to a result obtained for a sample taken from the same patient that had not been exposed to either heparin or heparinase.

Alternately, heparinase at a dosage of 0.01 IU heparinase/IU heparin can be intravenously injected into a mammalian body. Within fifteen minutes of the heparinase injection, the effects of the heparin on hemostasis will be neutralized.

The present invention will be further understood by reference to the following non-limiting examples.

EXAMPLE 1

Heparinase Preparation

100 L. *F. heparinum* was grown in a Chemap fermenter using a variation of the minimal media described by Galliher, et al., *Appl. Environ. Microbiol.* 41(2):360–365 (1981), the teachings of which are incorporated herein. The temperature was maintained at 23° C., and pH controlled to pH 7.0 by the appropriate addition of ammonium hydroxide. After 24 h incubation a volumetric heparinase activity of 2.5 IU/ml was achieved. The cells were concentrated by centrifugation and the heparinase released from the periplasmic space by a variation of the osmotic shock procedure described by Zimmermann, et al., U.S. Ser. No. 07/203,235, the teachings of which are incorporated herein. The osmolate was processed by cation exchange chromatography as described by Zimmermann, et al. The resulting heparinase fraction was loaded directly onto a cellufine sulfate column (5.0 cm i.d.×30 cm) and eluted with successive 1 L washes of 10 mM sodium phosphate, pH 7.0, 10 mM sodium phosphate, 200 mM NaCl, pH 7.0, 10 mM sodium phosphate, 400 mM NaCl, pH 7.0 and 10 mM sodium phosphate, 1000 mM NaCl, pH 7.0.

The results of the affinity chromatography step are shown in Table 1. Heparinase activity is recovered in the fraction eluting at 0.4 M NaCl while the anticoagulant moiety is in the unbound fraction. The heparinase recovered from this step is suitable for the intended use to eliminate heparin's effects on blood.

TABLE 1

Purification of heparinase by affinity chromatography using cellufine sulfate ™ (Amicon)

| sample | activity (IU) | specific activity (IU/mg) | anticoagulant activity* (aPTT ratio) |
|---|---|---|---|
| feed | 1670 | 28.3 | 2.0 |
| unbound fraction | 83.3 | ND | 3.4 |
| 0.2 M NaCl fraction | 0 | ND | 1.0 |
| 0.4 M NaCl fraction | 1470 | 41.7 | 1.0 |
| 1.0 M NaCl fraction | 0 | ND | 1.0 |

*anticoagulant activity is measured by incubating a known quantity of material with normal human plasma for 15 minutes at 4° C. and performing an aPTT test. The activity is expressed as a ratio of the aPTT of the plasma incubated with the material to the normal aPTT value for that sample (typically 24–28 seconds).

A further purification of the heparinase was achieved by hydroxylapatite column chromatography. The heparinase fraction collected from the cellufine sulfate chromatography step was dialyzed two times against ten volumes of 10 mM sodium phosphate, pH 7.0 and loaded onto a Biogel HTP ™ (BioRad) column (1.6 cm i.d. × 10 cm). The protein was eluted with a linear gradient of 10 to 250 mM sodium phosphate and 0 to 0.5 M sodium chloride over twenty column volumes. Heparinase was recovered in a single protein peak eluting at 16 mM sodium phosphate and 0.19 M sodium chloride. SDS-PAGE analysis of this material indicates that it approaches homogeneity (greater than 98%). A summary of the heparinase recovery steps showing purification data and the removal of the anticoagulant moiety is shown in Table 2. Homogeneous heparinase recovered from the hydroxylapatite step described above was similarly able to neutralize heparin in human blood and plasma indicating that no other protein contained in the cellurine sulfate preparation, beside heparinase, is required for this use.

TABLE 2

Purification of heparinase from *Flavobacterium heparinum* fermentations.

| sample | activity (IU) × 10³ | specific activity (IU/mg) | anticoagulant activity* (aPTT ratio) |
|---|---|---|---|
| fermentation | 83.30 | 0.58 | 1.5 |
| osmotic shock | 65.00 | 3.33 | 1.75 |
| cation exchange LC | 29.17 | 28.3 | 2.0 |
| affinity LC | 14.67 | 41.7 | 1.0 |
| hydroxylapatite LC | 9.83 | 75.0 | 1.0 |

*anticoagulant activity is measured by incubating a known quantity of material with normal human plasma for 15 minutes at 4° C. and performing an aPTT test. The activity is expressed as a ratio of the aPTT of the plasma incubated with the material to the normal aPTT value for that sample (typically 24–28 seconds).

EXAMPLE 2

Stabilization of Heparinase Preparation

The heparinase preparation is stable under normal manufacturing, shipping and clinical storage conditions for at least one year. Stability is in part a function of additives, most preferably ammonium sulfate. Several compounds have been examined for their ability to stabilize a soluble heparinase preparation. The results are shown in Table 3.

TABLE 3

Effect of additives on the stability of heparinase in solution at 23° C.

| Additive | quantity added (mg/IU heparinase) | t₁ (h) |
|---|---|---|
| water | ND | 4.00 |
| PBS (10 mM phosphate, 150 mM NaCl) | ND | 8.40 |
| dextran | 5.0 | 11.52 |
| β-cyclodextrin | 5.0 | 13.42 |
| sucrose | 5.0 | 9.12 |
| glucose | 5.0 | 12.48 |
| galactose | 5.0 | 15.05 |
| galactosamine | 5.0 | 36.00 |
| polyethylene glycol | 5.0 | 8.54 |
| albumin | 0.5 | 18.19 |
| cysteine | 0.1 | 38.40 |
| ammonium sulfate | 13.2 | 486.96 |
| calcium chloride | 0.6 | 196.80 |

Subsequently, the effect of varying quantities of lyophilized ammonium sulfate on coagulation was examined. Quantities of ammonium sulfate up to 2.5 mg/ml blood had no measurable effect on coagulation. As little as 0.2 mg ammonium sulfate per 1.5 IU heparinase is able to extend the half life of lyophilized enzyme to at least 200 days at 23° C. In this embodiment, 0.5 to 2.0 IU heparinase is lyophilized in the presence of 1.0 mg ammonium sulfate into tubes capable of containing 0.2 to 5.0 ml liquid. These may include a variety of tubes ranging from microtitre wells to 5.0 ml polypropylene test tubes. In other embodiments the heparinase-ammonium sulfate can be lyophilized directly into containers included in various commercially available hematological assay kits, into syringes which are used to collect the sample to be tested, into transfer pipets or into sterile vials with septum closures in which the preparation could be resolubilized prior to use as an injectable therapeutic agent.

EXAMPLE 3

Neutralization of Heparin in Samples for ACT Assays

ACT assays. The activated clotting time (ACT) assay is routinely employed in cardiovascular surgery to monitor the anticoagulant effects of heparin. As a functional measure of the intrinsic clotting pathway, ACT measurements are influenced by factors other than heparin. Cardiovascular procedures and extracorporeal circulation may lead to incidents of platelet dysfunction, hemodilution, disseminated intravascular coagulation, or hypercoagulation which alter the baseline clotting time during the course of an operation. Therefore, assuming a constant baseline ACT equivalent to the pre-operative value may lead to inaccurate conclusions concerning the administration of heparin or protamine. For example, hemodilution results in an extended ACT and may lead to an overestimate of the quantity of protamine required for neutralization. Conversely, hypercoagulation, induced by contact activation, results in a shortened ACT and may lead to an underestimate of the quantity of protamine required for neutralization.

The expeditious pre-treatment of samples to remove heparin prior to the determination of the ACT would allow for the procurement of baseline clotting information, even on sample taken from patients who have received heparin. 1.5 IU heparinase was lyophilized as described above into one channel of the dual test high range ACT cartridge manufactured by HemoTec, Inc. (Denver, Colo.). The resulting cartridge yields two test results: the activated clotting time of an untreated sample and the activated clotting time of a sample treated with heparinase. Freshly drawn blood was either directly assayed with these cartridges or incubated with 6 IU heparin/ml prior to the test. The results shown in Table 4 indicate that heparinase completely neutralized the heparin contained in the 6 IU/ml blood sample. The sample treated with both heparin and heparinase gave an identical result to a sample that had not been exposed to either reagent. Similar results are obtained over the range of 0–12 IU heparin/ml. The upper limit heparin dose observed in cardiovascular surgery is 6 IU/ml.

4) Has heparin rebound occurred post-surgically?

The results from a clinical study and interpretations of potential test results are show11 in Table 5.

TABLE 5

Uses of the heparinase activated clotting time test in cardiovascular surgery.

| Time of Test | ACT result | Heparinase ACT result | Condition | Recommended Action (19 cases) | study results |
|---|---|---|---|---|---|
| Pre-bypass | | | | | |
| | normal | normal | normal coagulation | none | 16/19 |
| | above normal | normal | heparin present | none | 0/19 |
| | above normal | normal | coagulopathy | further evaluation | 3/19 |
| On bypass | | | | | |
| | ≧450 | normal | anti-coagulated | none | 19/19 |
| | ≧450 | above normal | hemodilution | hemoconcentrate add coagulation factors and heparin | 0/19 |
| | below 450 | normal | insufficient anti-coagulant | add heparin | 0/19 |
| Post-protamine | | | | | |
| | normal | normal | adequate reversal | none | 4/19 |
| | above normal | above normal | hemodilution or coagulopathy | further evaluation add coagulation factors | 0/19 |
| | above normal | normal | heparin present | add protamine | 0/19 |
| | below normal | below normal | hyper-coagulation | anticoagulant therapy | 15/19 |
| | below normal | normal | hypercoagulation and heparin present | none | 0/19 |
| ICU | | | | | |
| | normal | normal | normal | none | ND |
| | above normal | normal | heparin rebound | add protamine | ND |
| | above normal | above normal | coagulopathy | further evaluation | ND |

Normal = 105–130 seconds

TABLE 4

Neutralization of heparin in whole human blood.

| sample | heparin (IU/ml) | heparinase (IU/ml) | ACT (sec) |
|---|---|---|---|
| whole blood | 0 | 0 | 131.3 ± 1.3 |
| whole blood | 0 | 1.5 | 128.0 ± 4.7 |
| whole blood | 6 | 0 | >999 |
| whole blood | 6 | 1.5 | 131.3 ± 4.3 |

This assay will provide the clinician with valuable information during cardiovascular surgery including answers to the following:
1) Is heparin present pre-surgically?
2) Has the baseline clotting time varied during the procedure?
3) Has protamine reversal of heparin been achieved?

EXAMPLE 5

Neutralization of Heparin in Clinical Samples for PT and aPTT Assays

PT/aPTT. Prothrombin time (PT) and activated partial thromboplastin time (aPTT) assays are routinely employed in the assessment of hemostatic function. PT is performed by adding a preparation of phospholipid, tissue factor and calcium to the patient's citrated plasma and determining the time required for a clot to form. This test measures the aggregate activity of factors VII, X, V and fibrinogen. The PT is often used to follow oral anticoagulant therapies, i.e., coumarin and anti-vitamin K drugs. The aPTT test is performed by adding a preparation of celite, phospholipid, and calcium to the patient's citrated plasma and determining the time required for a clot to form. This test measures the aggregate activity of factors XII, XI, IX, VIII, X, II, V and fibrinogen. The aPTT is commonly used as a coagulation screening test for factor dysfunction in hospitalized patients.

A method for determining heparin independent aPTT and PT measurements would aid in the evaluation of these results. In an analogous fashion to the development of the heparinase ACT test, the use of heparinase to provide baseline aPTT/PT information has been investigated. 1.5 IU heparinase was lyophilized into 1.5 ml polypropylene tubes as described above. This quantity of heparinase was able to completely reverse the effects of up to 1.0 IU/mL heparin in citrated human plasma, as shown in Table 6. The typical therapeutic heparin dose is 0.3 IU/mL.

TABLE 6

Neutralization of heparin in human plasma.

| sample | heparin (IU/ml) | heparinase (U/ml) | aPTT (sec) | PT (sec) |
| --- | --- | --- | --- | --- |
| human plasma | 0 | 0 | 25.7 ± 0.1 | 12.4 ± 0.3 |
| human plasma | 0 | 100 | 24.3 ± 0.1 | 12.2 ± 0.1 |
| human plasma | 0.5 | 0 | 87.6 ± 0.1 | 13.9 ± 0.3 |
| human plasma | 1.0 | 100 | 25.9 ± 0.2 | 12.7 ± 0.2 |
| human plasma | 1.0 | 0 | 299.0 ± 22 | 14.8 ± 0.1 |
| human plasma | 1.0 | 100 | 26.6 ± 0.2 | 12.4 ± 0.1 |

Whenever baseline coagulation data is desired, a 0.5 to 1.0 m/L plasma aliquot, can be added to the vial and gently mixed by inversion prior to standard coagulation analysis.

EXAMPLE 7

In Vivo Neutralization of Heparin

The previous unsuccessful attempts to neutralize heparin in vivo, reported by Klein, etal., (1982) and Langer, et al., (1982), appears to reflect the same phenomenon described above with respect to the *F. heparinum* anticoagulant moiety. Using heparinase purified by the method described herein, the in vivo investigation was repeated and complete heparin reversal was achieved within 15 minutes. The results are shown in FIG. 1.

A 4 kg rabbit was administered 250 IU/kg heparin extending the activated clotting time (ACT) from 180 to greater than 999 seconds. Within 5 minutes of heparin administration, 2.5 IU/kg heparinase was injected and the ACT monitored periodically over the following hour. Fifteen minutes after the heparinase injection, the ACT returned to baseline indicating a complete reversal of heparin's anticoagulant activity. The control rabbit, receiving the same amount of heparin, but no heparinase, returned to baseline ACT only after 1.5 hours.

This data indicates the potential for using direct heparinase injections as a method to reverse heparin in cardiovascular surgery.

Modifications and variations of the compositions and methods of use thereof of the present invention will be obvious to those skilled in the art from the foregoing detailed description. Such modifications and variations are intended to come within the scope of the appended claims.

We claim:

1. A heparinase isolated from *Flavobacterium heparinum*, said heparinase free of an anticoagulant component, having optimal activity at pH=6.5 to 7.0; salt concentration=0.1 M, and 37° C.,
   wherein the anticoagulant component does not bind to a polysulfated resin at pH 7.0, conductivity between 3 and 12 mmhos, and the heparinase does bind to a polysulfated resin at pH 7.0, conductivity between 3 and 12 mmhos.

2. The heparinase of claim 1 wherein the heparinase is isolated by affinity chromatography using the polysulfated resin.

3. The heparinase preparation of claim 2 wherein the heparinase is applied to the resin under conditions in which the heparinase is retained by the resin and the component inhibiting coagulation is not retained by the resin.

4. The heparinase of claim 3 wherein the heparinase is eluted from the resin by increasing the conductivity of the eluent such that the eluted heparinase fraction is free of the component inhibiting coagulation.

5. The heparinase of claim 1 wherein the heparinase is lyophilized and contains 0.5–1.0 mg ammonium sulfate/IU heparinase.

6. The heparinase of claim 5 wherein 0.05 to 3.0 IU anticoagulant free heparinase is lyophilized in the presence of 0.5–1.0 mg ammonium sulfate/IU heparinase into containers for the collection or incubation of blood or plasma samples.

* * * * *